United States Patent [19]

Sung et al.

[11] 4,080,199
[45] Mar. 21, 1978

[54] LATHE CUT DENTAL ALLOY POWDER

[75] Inventors: Pei Sung, Lawrenceville; Frederic James Schweder, Trenton, both of N.J.

[73] Assignee: Johnson & Johnson, New Brunswick, N.J.

[21] Appl. No.: 690,495

[22] Filed: May 27, 1976

[51] Int. Cl.$^2$ .................... C22C 30/02; C22C 30/04; C22C 30/06

[52] U.S. Cl. .................... 75/134 B; 75/.5 R; 75/134 C

[58] Field of Search ............ 75/.5 R, 134 N, 134 B, 75/134 C, 173 C, 169

[56] References Cited

U.S. PATENT DOCUMENTS

| | | | |
|---|---|---|---|
| 1,963,085 | 6/1934 | Gray | 75/173 C |
| 2,281,991 | 5/1942 | Poetschke | 75/173 C |
| 3,871,876 | 3/1975 | Asgar et al. | 75/169 |
| 3,975,192 | 8/1976 | Simpson | 75/169 |
| 3,985,558 | 10/1976 | Simpson | 75/169 |

*Primary Examiner*—W. Stallard

[57] ABSTRACT

A new dental alloy powder comprising lathe cut, homogeneous particles having a composition of 35 to 50 percent silver, 20 to 30 percent copper and 25 to 35 percent tin.

5 Claims, No Drawings

LATHE CUT DENTAL ALLOY POWDER

Amalgamatable dental alloys have been used for many years. These dental alloys, at least the conventional ones, contain from about 65 to 75 percent silver, 20 to 30 percent tin and up to 6 percent copper and 2 percent zinc. The conventional alloys, when amalgamated with mercury, form a substantial amount of gamma two phase which is corrosive and is detrimental to the final properties of fillings or restorations. In recent years new alloy compositions have been developed; basically, wherein the copper content is increased which in turn reduces the gamma two phase and improves the corrosion resistance of the amalgam.

Many conventional alloys contain non-uniform particles which are made from filing or grinding of the alloy ingot. In recent years alloys with spherical particles have been developed. Basically these alloys are made from an atomization process to form approximately spherical particles. There is some indication that spherical particles can make amalgams as strong or stronger than those produced from filings. Most dental alloys contain a relatively high percentage of silver; that is, 65 percent or more and hence, are quite expensive. If the amount or percentage of silver is reduced, then the particles are treated so there is higher silver content on the outer surface of the particle than inside the particle in order to allow the alloy to be suitably amalgamatable. This further process step in the manufacture of the alloy powder produces increased costs in the production of the alloy powder.

In attempting to reduce the gamma two phase and hence, reduce the corrosion of amalgams made with alloy powders; it is often the case that the final alloy is not lathe cuttable and cannot be produced by a filing or grinding technique but must be atomized to produce a spherical particle.

What we have discovered is a new dental alloy that is amalgamatable, easily handled, and has good initial and long-term compressive strengths. Our new dental alloy has a lower percentage of silver than most alloys and hence, is economical. Furthermore, our new dental alloy is unexpectedly grindable by standard lathe cutting techniques. In the process of making our new alloy homogeneous particles are formed and there is no necessity for an added step to increase the percentage of silver on the outside surface area of the particle. Amalgams made using our new alloy have no gamma two phase and hence, excellent corrosion properties. Also, the amalgams made with our new alloys have low tarnishing qualities. Our new amalgamatable dental alloy comprises lathe cut, homogeneous particles having a composition of from 35 to 50 percent silver, 20 to 30 percent copper and 25 to 35 percent tin. Preferably, our new alloy is a powder of lathe cut, homogeneous particles of from 41 to 46 percent silver, 22 to 25 percent copper and 26 to 29 percent tin.

In our new dental alloy, the powder comprises particles with each particle having a homogeneous composition and each particle having substantially the same composition. In the alloy, the silver to tin ratio will vary from about 1:1 to 2:1 whereas the tin to copper ratio will vary from about 5/6:1 to 1¾:1. If desired our new alloy may be pelletized and produced in pellet form by pressing the alloy in a pharmaceutical pill machine or it may be in the form of a loose powder. Our new alloy may also contain up to 2 percent zinc though it is preferred that the zinc be kept down to residual levels.

Our new alloys are amalgamatable with from about 46 to 58 percent mercury and preferably from about 48 to 52 percent mercury in mercury and powder combinations as is common with most alloys.

It is important in our new dental alloy to maintain the percent of silver within the 35 to 50 percent range and preferably within the 41 to 46 percent range. If more silver is present, our new alloy will not be effectively lathe cuttable. Furthermore, the higher the percentage of silver, the higher the cost of the alloy. If the amount of silver is reduced below 35 percent, the final alloy powder is not readily amalgamatable and handleable. The amount of tin in our new alloy is maintained between the 25 to 35 percent range. If more than 35 percent tin is present the final amalgam will contain some gamma two phase and have poor corrosion properties. If less than 25 percent tin is used in our new alloy, the resultant alloy will not be lathe cuttable. If more than 30 percent copper is used the final alloy is very difficult to amalgamate and, of course, if the copper is reduced below the 20 percent level, you have excess tin present and will again form the undesirable gamma two phase.

It is believed that the unexpected results of the present invention of a lathe cuttable, low silver content, gamma two free, homogeneous particle, alloy are derived from the silver, copper, tin compositions. It is believed that the silver-tin compound is of the $Ag_3Sn$ type and the copper-tin compound is of the $Cu_3Sn$ type which unexpectedly produce the desirable results obtainable with the alloys of the present invention.

The following examples demonstrate preferred alloy compositions in accordance with the present invention. It should be noted that all percentages are given in weight percent throughout this specification.

The following test methods are used to determine the various physical properties of the dental amalgams produced in the following examples.

GAMMA TWO DETERMINATION

A Phillips Electronic XRG-5000 X-ray generator with step diffractrometer is used in determining the gamma two phase. A copper radiation is used for all studies. Polished amalgamated samples are used in all studies. The surfaces of the amalgamated sample are polished under cold water by using successively finer grit papers. The polished samples are scanned at 2° ($2\theta$) per minute from 28 degrees to 56 degrees ($2\theta$). Particular attention is paid to the regions corresponding to the locations of the gamma two ($Sn_{7-8}Hg$) peaks.

AMALGAM SET TIME

This test is based on the principle that when the amalgam no longer can be reformed into a ball it has reached its set time. 0.60 grams of mercury and 0.60 grams of alloy powder are placed in a capsule and triturated for ten seconds with a Toothmaster, Model 300 Amalgamator. A stopwatch is started and any pestle used with the capsule removed. The capsule is replaced in the amalgamator and the mull button pressed to form a ball. One and one-half minutes is allowed to elapse and the mull button pressed again for one second. Every 30 seconds thereafter the mull button is pressed for one second until the sample crumbles for the first time. The first crumble occurs mid-way through the final set time. The mull button is pressed for three seconds to form a ball again. The mull button is pressed for one second every thirty seconds thereafter until the second ball crumbles. The elapsed time between the end of trituration and the crumbling of the ball the second time is recorded as the set time.

AMALGAM COMPRESSIVE STRENGTHS 0.63 grams of mercury and 0.63 grams of alloy powder are placed in a capsule with a pestle and triturated for ten seconds using a Toothmaster Amalgamator. The capsule is opened, the pestle removed, and the amalgam poured into a die cavity. A plunger is placed on top of the amalgam and 2000 pounds per square inch of pressure applied. The load is applied and released a number of times to compact and press the amalgam. Excess mercury is brushed away and the sample ejected from the die. The sample is four millimeters in diameter and eight millimeters in length. Samples made as described above are conditioned for one hour and 24 hours in an oven at 37° C. The resultant conditioned cylindrical sample is placed on its vertical Axis on the compression cell of a compression testing machine and compressive strength tested. The compression testing machine used is an instron Tester Model TMA1115.

EXAMPLE I

Ninety-one grams of silver, 57 grams of tin, 50 grams of copper and 2 grams of zinc are melted together in an induction furnace at 1100° C. The composition of the final melt contains 46.8 percent silver, 28.8 percent tin, 24.0 percent copper and approximately 0.4 percent zinc. The liquid metal is poured into a 1 inch diameter graphite mold and quenched to room temperature in water. The resulting ingot is mounted on a mechanical lathe at a rotating speed of 80 rpms. A cutting tool at a 30° angle is used to cut the ingot at a feeding rate of .0015 inches per revolution. The filings are ball milled in a stainless steel jar with stainless steel balls for 2½10 hours. The powder is screened through a 400 mesh, a 20 micron and ten micron screens. The −400 mesh, −20 micron and −10 micron powders are annealed at 350° C for 2½ to 3 hours. The following table gives the results of evaluating the gamma two phase, set time and compression strength for the various particle size alloys of this Example.

TABLE I

|  | −400 Mesh | −20 Micron | −10 Micron |
| --- | --- | --- | --- |
| Powder to Mercury Ratio | 1:1 | 1:1 | 1:1 |
| Gamma Two Phase | No | No | No |
| Setting Time | ~2½ min. | ~2 min. | ~2 min. |
| One Hour Compression Strength | 24,636 psi | 31,022 psi | 34,053 psi |
| 24 Hour Compression Strength | 50,636 psi | 56,762 psi | 63,281 psi |

EXAMPLE II

The less than ten micron alloy powder of Example I is mixed with 25 percent silver-copper-eutectic powder containing 72 percent silver and 28 percent copper having a medium particle size of 28 microns. The sample is triturated with mercury as previously described and its various physical properties measured and determined as given in the following table.

TABLE II

|  | Alloy of Example I + 25% Silver-Copper-Eutectic |
| --- | --- |
| Particle Size of Melt | −10 microns |
| Powder to Mercury Ratio | 1:1 |
| Gamma Two Phase | No |
| Setting Time | ~2 minutes |
| One Hour Compression Strength | 28,212 psi |
| 24 Hour Compression Strength | 65,641 psi |

The present invention has been described in terms of presently known preferred embodiments and it is intended the compositions which may depart from those presently preferred which demonstrate the novel advantages of use are to be included in the scope of the appended claims.

What is claimed is:
1. A corrosion resistant, readily amalgamatable dental alloy comprising lathe cut particles with each particle consisting essentially of a homogeneous mixture of, by weight, 41 to 46 percent silver, 22 to 25 percent copper, 26 to 29 percent tin and less than 2% zinc.
2. A dental alloy according to claim 1 wherein the particles are less than 400 mesh in size.
3. A dental alloy according to claim 1 wherein the silver to tin ratio is from 1:1 to 2:1.
4. A dental alloy according to claim 1 wherein the tin to copper ratio is 5/6:1 to 1¾:1.
5. A dental alloy according to claim 1 wherein the silver to tin ratio is 1:1 to 2:1 and the tin to copper ratio 5/6:1 to 1¾:1.

* * * * *

UNITED STATES PATENT AND TRADEMARK OFFICE
CERTIFICATE OF CORRECTION

PATENT NO. : 4,080,199
DATED : March 21, 1978
INVENTOR(S) : Pei Sung and Frederic James Schweder It is certified that error appears in the above-identified patent and that said Letters Patent are hereby corrected as shown below:

At Column 1, Line 28, "," should be -- . --.
At Column 3, Line 41, "21/210" should be -- 2 1/2 --.

Signed and Sealed this

Seventh Day of November 1978

[SEAL]

Attest:

RUTH C. MASON
Attesting Officer

DONALD W. BANNER
Commissioner of Patents and Trademarks